(12) United States Patent
Garcia et al.

(10) Patent No.: US 7,498,306 B2
(45) Date of Patent: Mar. 3, 2009

(54) PEPTIDES BINDING TO THE PHOSPHATASE 2A PROTEIN

(75) Inventors: Alphonse Garcia, Paris (FR); Frederic Dessauge, Paris (FR); Xavier Cayla, Rochecorbon (FR); Angelita Rebollo, Paris (FR)

(73) Assignee: Institut Pasteur, Paris (FR)

( * ) Notice: Subject to any disclaimer, the term of this patent is extended or adjusted under 35 U.S.C. 154(b) by 336 days.

(21) Appl. No.: 11/107,814

(22) Filed: Apr. 18, 2005

(65) Prior Publication Data

US 2007/0065410 A1 Mar. 22, 2007

Related U.S. Application Data

(63) Continuation of application No. PCT/FR03/03018, filed on Oct. 13, 2003.

(30) Foreign Application Priority Data

Oct. 16, 2002 (CA) ................................. 2408207

(51) Int. Cl.
*A61K 38/00* (2006.01)
*A61K 48/00* (2006.01)
*C07K 1/00* (2006.01)
*C07K 14/00* (2006.01)
*C07K 14/01* (2006.01)
*C07K 14/075* (2006.01)
*C07K 16/18* (2006.01)
*C07K 17/00* (2006.01)
*C12N 5/06* (2006.01)
*C12N 5/16* (2006.01)
*C12N 15/34* (2006.01)
*C12N 15/86* (2006.01)
*G01N 33/68* (2006.01)

(52) U.S. Cl. .............................. 514/12; 514/2; 514/13; 514/14; 514/15; 514/16; 530/300; 530/324; 530/325; 530/326; 530/327; 530/328; 530/350; 435/4; 435/6; 435/41; 435/42; 435/252.3; 435/254.2; 435/330

(58) Field of Classification Search ........................ None
See application file for complete search history.

(56) References Cited

U.S. PATENT DOCUMENTS

| 5,789,201 A * | 8/1998 | Guastella .................... 435/69.1 |
| 5,856,171 A * | 1/1999 | Korsmeyer ................ 435/254.2 |
| 2001/0018211 A1* | 8/2001 | Chinnadurai ................. 435/330 |
| 2003/0176671 A1* | 9/2003 | Reed et al. .................. 536/23.1 |
| 2006/0014930 A1* | 1/2006 | Garcia et al. ................. 530/326 |

FOREIGN PATENT DOCUMENTS

| WO | WO 98/01563 | 1/1998 |
| WO | WO 03/011898 | 2/2003 |

OTHER PUBLICATIONS

Marcellus RC, Chan H, Paquette D, Thirlwell S, Boivin D, Branton PE, Induction of p53-independent apoptosis by the Adenovirus E4orf4 protein requires binding to the B-alpha subunit of protein phophatase 2A, Journal of Virology, Sep. 2000, 74(17): 7869-7877.*
Rudinger J, Characteristics of the amino acids as components of a peptide hormone sequence, Peptide Hormones, Edited by J.A. Parsons, Jun. 1976.*
Designing Custom Peptides, SIGMA Genosys, http:/www.sigma-genosys.com/peptide_design.asp, accessed Dec. 2004.*
Berendsen HJC, A Glimpse of the Holy Grail?, Science, 1998, 282: 642-643.*
Biochemistry text book, 2$^{nd}$ Edition, by Voet and Voet, John Wiley & Sons, Inc., 1995.*
Miroshnikov et al, Zhurnal Obshschei Khimli, vol. 40(2), pp. 429-443, 1970 with English abstract.
Shtrichman et al, Proc. Nat. Acad. Sci. USA, vol. 96, No. 18, pp. 10080-10085, 1999.

* cited by examiner

*Primary Examiner*—Anish Gupta
*Assistant Examiner*—Julie Ha
(74) *Attorney, Agent, or Firm*—Oblon, Spivak, McClelland, Maier & Neustadt, P.C.

(57) ABSTRACT

The invention relates to novel synthetic or natural E4orf4 or Bcl-2 peptides particularly useful in antitumoral, antiviral and antiparasitic treatments, said peptides being less than 30 amino acids long and binding in vitro to a phosphatase 2A protein holoenzyme or one of its subunits. The invention also relates to polynucleotides encoding the novel peptides, vectors expressing same, as well as antibodies identifying same and probes identifying transcripts thereof.

20 Claims, 2 Drawing Sheets

SEQUENCE LISTING

<160> NUMBER OF SEQ ID NOS: 15

<210> SEQ ID NO 1
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 1

Arg Glu Leu Gly Ser Met Leu Glu Ser Pro Met Glu Phe Leu Phe Asp
1               5                   10                  15

Thr Ile Asp Asp Val Thr Ala Ser
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 2

Leu Gly Ser Met Leu Glu Ser Pro Met Glu Phe Leu Phe Asp Thr Ile
1               5                   10                  15

Asp Asp Val Thr Ala Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Ser Met Leu Glu Ser Pro Met Glu Phe Leu Phe Asp Thr Ile Asp Asp
1               5                   10                  15

Val Thr Ala Ser
            20

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

His Phe Lys Gly Thr Leu Ile Lys Glu Ile Ser Asp Val Val Asn Asn
1               5                   10                  15

```
<210> SEQ ID NO 5
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 5

Ala Phe Arg Gly Arg Glu Val Thr Val Ser Leu Leu Glu Val Phe Ser
1               5                   10                  15

Phe Cys

<210> SEQ ID NO 6
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 6

Val Lys Lys Lys Ile Lys Arg Glu Ile Lys Ile Ser Met Leu Glu
1               5                   10                  15

Ser Pro Met Glu Phe Leu Phe Asp Thr Ile Asp Asp Val Thr Ala Ser
                20                  25                  30

<210> SEQ ID NO 7
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 7

Ala Arg Thr Ser Pro Leu Gln Thr Pro Ala Ala Pro Gly Ala Ala Ala
1               5                   10                  15

Gly Pro Ala Leu
                20

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 8

Arg Phe Ala Thr Val Val Glu Glu Leu Phe Arg Asp Gly Val Asn Trp
1               5                   10                  15

<210> SEQ ID NO 9
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 9

Arg Pro Leu Phe Asp Phe Ser Trp Leu Ser Leu Lys Thr Leu Leu Ser
1               5                   10                  15

Leu Ala Leu Val Gly Ala
                20

<210> SEQ ID NO 10
```

-continued

<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Pro Leu Gln Thr Pro Ala Ala Pro Gly Ala Ala Ala Gly Pro Ala Leu
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Leu Phe Asp Phe Ser Trp Leu Ser Leu Lys Thr Leu Leu Ser Leu Ala
1               5                   10                  15

Leu Val Gly Ala
            20

<210> SEQ ID NO 12
<211> LENGTH: 375
<212> TYPE: DNA
<213> ORGANISM: Canine adenovirus type-2

<400> SEQUENCE: 12
atggcccacc atcgtctgcc ccgcgtttgt gtaaagggca ttattcattt tgaggaagat      60
tttgttagag agcttggatc aatgctggag tctcctatgg agtttctctt cgacaccatt     120
gatgatgtta ctgcttctat attttgtgaa agcatgttta aggctgttga taaaaacaag     180
cctgggatta cttttaaggt ggtcttttac tctcagcttg gttttgagta tgatgatgct     240
cttgcacatt ttaaaggcac tttaattaaa gaaatttctg acgttgttaa taatcacccct    300 aatgtaaaca atgcttttag aggaagggag attgtcactg tatctttgtt agaagtgttt     360 agttttttgtt cataa                                                     375

<210> SEQ ID NO 13
<211> LENGTH: 128
<212> TYPE: PRT
<213> ORGANISM: Canine adenovirus type-2

<400> SEQUENCE: 13

Met Ala His His Arg Leu Pro Arg Val Cys Val Lys Gly Ile Ile His
1               5                   10                  15

Phe Glu Glu Asp Phe Val Arg Glu Leu Gly Ser Met Leu Glu Ser Pro
                20                  25                  30

Met Glu Phe Leu Phe Asp Thr Ile Asp Asp Val Thr Ala Phe Thr Ser
            35                  40                  45

Ile Phe Cys Glu Ser Met Phe Lys Ala Val Asp Lys Asn Lys Pro Gly
    50                  55                  60

Ile Thr Phe Lys Val Val Phe Tyr Ser Gln Leu Gly Phe Glu Tyr Asp
65                  70                  75                  80

Asp Ala Leu Ala His Phe Lys Gly Thr Leu Ile Lys Glu Ile Ser Asp
                85                  90                  95

Val Val Asn Asn His Pro Asn Val Asn Asn Phe Thr Ala Phe Arg Gly
            100                 105                 110

Arg Glu Ile Val Thr Val Ser Leu Leu Glu Val Phe Ser Phe Cys Ser 115                 120                 125

<210> SEQ ID NO 14
<211> LENGTH: 618
<212> TYPE: DNA
<213> ORGANISM: Artificial Sequence
<220> FEATURE:
<223> OTHER INFORMATION: Synthetic DNA

<400> SEQUENCE: 14

```
atggcgcacg ctgggagaac ggggtacgac aaccgggaga tagtgatgaa gtacatccat      60
tataagctgt cgcagagggg ctacgagtgg gatgcgggag atgtgggcgc cgcgcccccg     120
ggggccgccc ccgcaccggg catcttctcc tcccagcccg gcacacgcc ccatccagcc      180
gcatcccgcg acccggtcgc caggacctcg ccgctgcaga ccccggctgc ccccggcgcc     240
gccgcgggc ctgcgctcag cccggtgcca cctgtggtcc acctggccct ccgccaagcc     300
ggcgacgact tctcccgccg ctaccgcggc gacttcgccg agatgtccag ccagctgcac     360
ctgacgccct tcaccgcgcg gggacgcttt gccacggtgg tggaggagct cttcagggac     420
ggggtgaact gggggaggat tgtggccttc tttgagttcg gtggggtcat gtgtgtggag     480
agcgtcaacc gggagatgtc gccctggtg acaacatcg ccctgtggat gactgagtac       540
ctgaaccggc acctgcacac ctggatccag gataacggag gctgggtagg tgcatctggt     600
gatgtgagtc tgggctga                                                   618
```

<210> SEQ ID NO 15
<211> LENGTH: 211
<212> TYPE: PRT
<213> ORGANISM: Artificial Sequence
<220> FEATURE:
<223> OTHER INFORMATION: Synthetic Peptide

<400> SEQUENCE: 15

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Phe Thr Pro
        35                  40                  45

Gly Ile Phe Ser Ser Gln Pro Gly His Thr Pro His Pro Ala Ala Ser
    50                  55                  60

Arg Asp Pro Val Ala Arg Thr Ser Pro Leu Gln Thr Pro Ala Ala Pro
65                  70                  75                  80

Gly Ala Ala Ala Gly Pro Ala Leu Ser Pro Val Pro Pro Val Val His
                85                  90                  95

Leu Ala Leu Arg Gln Ala Gly Asp Asp Phe Phe Thr Ser Arg Arg Tyr
            100                 105                 110

Arg Gly Asp Phe Ala Glu Met Ser Ser Gln Leu His Leu Thr Pro Phe
        115                 120                 125

Thr Ala Arg Gly Arg Phe Ala Thr Val Val Glu Glu Leu Phe Arg Asp
    130                 135                 140

Gly Val Asn Trp Gly Arg Ile Val Ala Phe Phe Glu Phe Gly Gly Val
145                 150                 155                 160

Met Cys Val Glu Ser Val Asn Phe Thr Arg Glu Met Ser Pro Leu Val
                165                 170                 175

Asp Asn Ile Ala Leu Trp Met Thr Glu Tyr Leu Asn Arg His Leu His
            180                 185                 190

```
Thr Trp Ile Gln Asp Asn Gly Gly Trp Val Gly Ala Ser Gly Asp Val
        195                 200                 205

Ser Leu Gly
    210
```

PEPTIDES BINDING TO THE PHOSPHATASE 2A PROTEIN

CROSS-REFERENCE TO RELATED APPLICATIONS

The present application is a continuation of International Application PCT/FR03/03018, filed on Oct. 13, 2003, which claims priority to CA 2,408,207, filed on Oct. 16, 2002.

FIELD OF THE INVENTION

The present invention concerns peptides binding a phosphatase 2A protein, an important target for the control of apoptosis, in particular in cancer cells, as well as for the control of viral and parasitic infections.

BACKGROUND OF THE INVENTION

Given the role of the peptides of the invention in modulating the activity of the cellular protein phosphatase 2A, it is important to mention the present state of the art on protein phosphatases 2A, their physiological role and their interactions with some cellular, viral or parasitic proteins.

Cell physiology is controlled in part by modulation of the phosphorylation state of proteins. The phosphorylation state of cellular proteins depends on the antagonistic action of the protein kinases that phosphorylate them and the protein phosphatases that dephosphorylate them.

Protein phosphatases are divided into two main groups: tyrosine phosphatases and serine/threonine phosphatases. Serine/threonine phosphatases are classified into two categories depending on the specificity of their substrate and their sensitivity to certain inhibitors, the type 1 and type 2 phosphatases (PP1 and PP2). The type 2 phosphatases are again divided into different classes, including phosphatase 2A (PP2A), phosphatase 2B (PP2B) or calcineurin which activity is regulated by calcium, and phosphatase 2C (PP2C) which activity is magnesium-dependent.

In vivo, the serine/threonine protein phosphatases PP1 and PP2A form two families of many ubiquitously expressed holoenzymes. These holoenzymes are produced by the specific interaction between their catalytic subunits (PP1c and PP2Ac) and a wide variety of regulatory subunits. Moreover, these holoenzymes are involved in targeting and/or regulation of phosphatase activity (for recent review, see Garcia A. et al., PP1 et PP2A, des ser/thr phosphatases au coeur de l'apoptose (2001) Med/Sci 17, 1214-1216).

It is now known that type 2A phosphatases are very conserved throughout evolution and are potentially activated during regulation of various biological processes. The PP2A enzymes have clearly been involved in transcription control, cell cycle control, and viral transformation. Moreover, the PP2As are the targets of different viral or parasitic proteins, thus suggesting a role for PP2As in host-pathogen interactions.

The PP2As are oligomeric complexes (holoenzymes), each of said complexes comprising a catalytic subunit C and one or two regulatory subunits, (A) and (B). The structure of subunit (A) consists of 15 imperfect repeats of a conserved 38 to 40-amino acid sequence, some subunits (A) interacting with subunits (B) and (C). Subunits (A) and (C), conserved throughout evolution, form the base structure of the enzyme and are constitutively expressed. By contrast, subunits (B) form a family of regulatory proteins differentially expressed and with no common structure between one another (Cohen P. *The structure and regulation of protein phosphatases*. Annu. Rev. Biochem. 1989; 58:453-508). Therefore, the protein phosphatases 2A are present in vivo under two different forms: a dimeric form (AC) and a trimeric form (ABC). Subunits (B) regulate the phosphatase activity and the specificity towards the substrate. The existence of multiple forms of PP2A correlates with distinct and varying functions of the PP2As in vivo.

Recently, it has been found that different non cellular proteins, and in particular viral and parasitic proteins, are involved in the modulation of some specific activities of protein phosphatases 2A.

Different strategies involving the PP2A are adopted by the viruses to facilitate their replication and survival in the host cell. For example, the parainfluenza virus incorporates, in its viral particle, the PKC ζ protein, a protein of cellular origin under the control of the PP2A. This virus can thus perturb the host proteins' phosphorylation and facilitate its own replication (B. P. Gupta et al. Cellular protein kinase C ζ regulates human parainfluenza virus type 3 replication. Proc. Natl. Acad. Sci. USA 1995; 92:5204-8).

Many DNA viruses with a transforming potential, such as papovaviridae or adenoviruses, as well as some retroviruses, such as the type 1 human immuno-deficiency virus (HIV-1), code for proteins that interact directly with some host PP2As. All these viruses include proteins that, even though they are structurally different from one another, interact with some holoenzymes and modify the phosphatase activity thereof.

More particularly, the E4orf4 protein of adenoviruses binds to a heterotrimeric PP2A and, more precisely, to a regulatory subunit (B), thus leading to a decrease in transcription of JunB in the infected cell. This effect could play an important role during viral infection by regulating the apoptotic response in infected cells. Interestingly, the interaction between E4orf4 and PP2A induces apoptosis of transformed cells in a p53-independent manner (Shtrichman R. et al. *Adenovirus type 5 E4 open reading frame 4 protein induces apoptosis in transformed cells*. J. Virol. 1998; 72:2975-82).

The oncogenic DNA viruses of the Papovaridae family, including SV40 and the polyoma virus, induce cell transformation. PP2A interacts with the "small T" antigens of SV40 and the "small T" and "middle T" of the polyoma virus. The interactions between these viral proteins and the PP2A are clearly involved in viral transformation. Finally, the transcriptional control, a process normally led in the cell by the different factors which specifically bind to promoter regulatory sequences, represents probably the most important mechanism in viral expression control by PP2A. Therefore, PP2A is a negative regulator of numerous transcription factors, namely involved in the cell growth and proliferation processes, including AP1/SRE, NF-kB, Sp1 and CREB (Waszinski, B. E. et al. *Nuclear protein phosphatase 2A dephosphorylates protein kinase A-phosphorylated CREB and regulates CREB Transcriptional stimulation*. Mol. Cell Biol. 1993:13, 2822-34). The viral control of these transcription factors could allow to modulate viral transcription.

Vpr, the viral protein of HIV-1, interacts in vitro with PP2A and stimulates the catalytic activity thereof (Tung L, et al. *Direct activation of protein phosphatase 2A0 by HIV-1 encoded protein complex Ncp7:vpr*. FEBS Lett 1997; 401: 1997-201). Vpr can induce a G2 arrest in infected cells by inhibiting the activation of the p34cdc2-cyclin B complex. In addition, Vpr interacts with the Sp1 transcription factor and is a weak trans-activator of the Sp1-dependent transcription of HIV-1. Therefore, the Vpr protein of HIV-1, which is incorporated within the virion, would be involved in vivo in the initiation of viral transcription, an essential step in regulating the expression of the Tat transcription factor (a major regulator in the transcription coded by the HIV-1 virus).

Unlike the protein kinases that have a well-established role in parasitic infections, serine/threonine phosphatases have only recently been recognized as potentially important regulators in parasitology.

The absence of common motifs for the bulk of proteins that interact with PP2A impedes the simple identification by bioinformatics of peptide motifs directly involved in the binding of these proteins with PP2A.

However, given the major role of protein phosphatases 2A in virus-host or parasite-host interactions as detailed hereinabove, it will be understood that there is a great interest in identifying the binding sites of viral or parasitic proteins with PP2A holoenzymes or one of their subunits, to identify new therapeutic targets for these viral or parasitic pathogens.

The type 1 and type 2A serine/threonine phosphatases (PP1 and PP2A) represent new potentially important targets for apoptotic control, namely in cancer cells, as well as for the control of viral or parasitic infections (for review, see A. Garcia et al. (2000) *Protein Phosphatase 2A: a definite player in Viral and parasitic regulation*. Microbes Inf. 2,401-407; Et X. Cayla et al. (2000). *La Protéine Phosphatase 2A: une nouvelle piste pour l'étude des virus et des parasites*. Méd/Sci 16, 122-127). More particularly, PP1/PP2A would play a crucial role in the regulation of anti-apoptotic Bcl-2 proteins and cell survival (Garcia A et al., *PP1 et PP2A des ser/thr phosphatases au coeurde l'apoptose* (2001). Med/Sci 17, 1214-1416; Ayllón, V. et al. (2000). *Protein phophatase 1- is a Ras-activated Bad phosphatase that regulates IL-2 deprivation-induced apoptosis*. EMBO J. 19, 2237-2246, Ayllón, V. et al. (2000) *Bcl-2 targets protein phosphatase 1 alpha to Bad*. J. Immunol. 15; 166:7345-7352). Identification of peptides that interact with PP2A could help to produce new drugs susceptible to block, by competitive inhibition, cellular mechanisms induced by viral or parasitic proteins, by their interaction with PP2A and, in particular, the mechanisms of infection, pathogen proliferation and neoplastic cell transformation.

In particular, PP2A activation after interaction with the E4orf4 adenoviral protein induces apoptosis in transformed cells (Shtrichman R, et al. (2000) Oncogene. 19, 3757-3765). This specific effect requires an interaction with the B alpha (Bα) subunit of PP2A (Marcellus et al. J Virol. (2000) 74:7869-7877)/Goedert et al. J.Neurochem (2000) 75,2155-2162)). All of the above-mentioned observations suggest the hypothesis that the interaction of peptides mimicking the ABC1 and/or A3 site with PP2A could lead to apoptosis of transformed cells.

WO9801563 and WO0104329 A1 describe the human E4orf4 protein and its role in induction of apoptosis in tumour cells, particularly when this protein is expressed via an adenoviral vector. WO0104629 A1 relates to the modulating and mimetic polypeptides E4orf4 and PP2A, capable to induce a selective cell death. This document discloses an invention which relates to the ability of the E4orf4 adenoviral protein to induce the death of neoplastic cells but not of non neoplastic cells. Moreover, WO9801563 A2 relates to the E4orf4 and E4orf6 adenoviral proteins, destined to induce cell death. Finally, the patent application No. FR 0110139 describes peptidic compounds that can bind to PP2A.

Also, the Bcl-2 protein family which, in mammals, comprises about twenty members, can be divided into three subfamilies including:

the anti-apoptotic members (of the Bcl-2 type itself) which all present at least four conserved motifs, called "BH1 to BH4" for "Bcl-2 Homology domain", are necessary to the function of cell survival. The BH4 motif comprises the interaction domain with the Raf and Apaf-1 proteins, and with calcineurine;

the pro-apoptotic members of the Bax type do not present a BH4 domain; and the pro-apoptotic members of the Bad type only present one BH3 domain.

Mutagenesis experiments show that the anti-apoptotic activity of Bcl-2 requires its phosphorylation at the specific residue serine 70 that, when replaced by alanine, inhibits survival. Moreover, the work from Dr. May's team (USA) (2001, Vol. 15, No. 4, pp 515-522) suggests that, in the presence of IL-3, PP2A can transitorily associate itself with Bcl-2. The use of a point mutant (wherein one alanine residue replaces the serine 70) indicates that the binding of PP2A to Bcl-2 requires the presence of serine 70 which, consequently, could belong to the binding site. The authors thus suggest a dynamic regulatory mechanism whereby PP2A would be a Bcl-2 phosphatase, antagonistic to Bcl-2 kinases, for example the PKCs (for discussion, see Garcia A. et al., *PP1 et PP2A des ser/thr phosphatases au Coeurde l'apoptaose* (2001). Med/Sci 17, 1214-1216).

The presence of these Bcl-2 peptides inside the cell could thus regulate the phosphorylation, consequently the activity, of Bcl-2 which in turn could block the development of Bcl-2-dependent tumours.

There is thus a need, at the level of antitumour, antiviral and antiparasitic treatments, for peptides derived from E4orf4 and Bcl-2 sequences which bind to PP2A or one of its subunits.

SUMMARY OF THE INVENTION

The present invention takes an interest in E4orf4 and Bcl-2 peptides of small dimension that bind a PP2A holoenzyme or one of its sub-units. Contrary to E4orf4 and Bcl-2 native proteins or polypeptidic domains of greater dimensions, peptides of small dimensions have the advantage of being easily synthesized, by chemical way or in cellular systems, with a high yield and a reduced cost. Peptides of the invention present, moreover, the advantage of being more accessible and of being more easily transferred in the cytoplasm or in the nucleus of the cells using appropriate vectors, for a therapeutic use.

The invention follows from the identification of E4orf4 and Bcl-2 peptides, which have a dimension less than 30 amino acids, and especially peptides having a dimension less than 20 amino acids, interacting in vitro with a purified phosphatase 2A protein holoenzyme or one of its subunits.

In particular, the inventors have identified by the "SPOT synthesis" technique decribed by Frank and Overwing (*Methods in Molecular Biology*, 1996, vol. 66: 149-169, *Epitope Mapping Protocols*, G.E. Morris Humana Press Inc., Totowa N.J.) the binding sites of the E4orf4 (canine adenovirus type 2) and Bcl-2 proteins interacting with a PP2A holoenzyme or one of its subunits.

On the one hand, the peptides of the invention are peptides having a dimension less than 30 amino acids, interacting in vitro with a purified PP2A holoenzyme or one of its subunits, said peptides being derived from the E4orf4 protein (canine adenovirus type 2) and Bcl-2 protein. Antagonists derived from these peptides and selected because they inhibit the interaction of viral or parasitic proteins with a specific PP2A holoenzyme could thus constitute new antitumor, antiviral or antiparasitic agents On the other hand, the invention also concerns a peptide comprising a 12 amino acid sequence of the *Theileria parva* Ckα 2 protein (FD6) capable of interacting with the PP2A sub-unit A and to penetrate in a Hela cell(Garcia, A. et al. (2000). The invention is further concerned with the sequence corresponding to the interaction site of the PP2A with the Bα sub-unit of the PP2A 1-B site (cf. table 1). This peptide could penetrate in cells and, like the E4orf4 protein of the human adenovirus, could interact with PP2A and provoke apoptosis in cancer cells without affecting the normal cells.

The identification method described in application FR no. 0110139 filed on Jul. 27, 2001 in the name of the Applicant, comprises the following steps which consist of:
a) spotting, on a support, E4orf4 or Bcl-2 peptides which there sequence derived respectively from the viral E4orf4 protein or the cellular Bcl-2 protein, each spot corresponding to a deposit of a peptide with a defined sequence,
b) contacting the solid support with a solution containing a phosphatase 2A holoenzyme or one of its subunits under conditions allowing said peptides present onto the support, to bind the holoenzyme or one of its subunits, and,
c) identifying on the solid support the E4orf4 peptide or the Bcl-2 peptide onto which said phosphatase 2A holoenzyme or one of its subunits is bound.

According to step a), different peptides are spotted on a support at defined positions (spot), each position corresponding to a specific peptide sequence and the whole then forming a two dimension peptide array.

Diffrent preparaton methods of such arrays have been recently described (for review, see Figeys et Pinto, 2001 *Electrophoresis* 22: 208-216; and Walter et al., 2000 *Curr Opin Microbiol* 3: 298-302). These methods comprise in general the covalent binding of peptides on a support, in particular with the aid of chemical linkers. For instance, one skilled in the art could refer to the "SPOT synthesis" technique which consists of directly synthesize on a cellulosic membrane, peptides comprising up to 20 residues (Frank and Overwing, *Methods in Molecular Biology,* 1996, vol. 66: 149-169, *Epitope Mapping Protocols,* G.E. Morris Humana Press Inc., Totowa N.J.).

Generaly any method could be used from the moment that such a method allows the production of such a peptide array, E4orf4 or Bcl-2, spotted on a solid support, useful for detecting specific interaction between spotted peptides and the PP2A holoenzyme or one of its subunits.

The totality of the spotted E4orf4 and Bcl-2 peptide sequences cover the complete sequence of the corresponding viral or cellular protein. Therefore, the process allows to test in a single step the complete sequence, the latter being <<split>> into a number of defined peptides, generally of overlapping sequences.

The spotted peptides have a dimension less than 20 amino acids, and preferably, less than 15 amino acids.

The peptides may also be spotted on a cellulosic membrane.

The array thus obtained is contacted at step b), with a phosphatase 2A protein holoenzyme or one of its subunits.

By "phosphatase 2A protein holoenzyme", it is meant any dimeric (AC) or heterotrimeric (ABC) complex, purified from a cellular extract or reconstituted following purification of the two subunits (A) and (C) of a phosphatase type (2A) protein or, if necessary, from the subunit (B). the phosphatases type (2A) proteins are preferably derived from mammals.

The supports are incubated, for instance, in a buffered solution comprising the purified phosphatase proteins or one of their purified subunits. A usable buffered solution is TBS (TRIS BUFFER SALINE) containing 5% of skim milk powder and 3% of BSA.

The peptide onto which the phosphatase 2A protein holoenzyme is bound, is identified generally by direct or indirect labelling of the phosphatase protein and identification of spots where the labelled protein is bound. The binding of the PP2A or one of its subunits on one of the peptidic spots may be shown, in particular, with antisera, according to known techniques with regards to Western Blot or ELISA, following the incubation of the support containing the peptide array with an antibody raised against the subunits (A) or (B) or (C) or a mixture of antibodies raised against the PP2A subunits (A), (B) or (C).

The use of the <<SPOT synthesis>> method described in FR no. 0110139 has lead to the identification E4orf4 and Bcl-2 peptides, useful especially in anti-tumor, antiviral and antiparasitic treatments, having a dimension less than 30 amino acids, even less than 20 amino acids, these peptides being able to bind in vitro a phosphatase 2A protein holoenzyme or one of its subunits.

The invention is thus concerned with a E4orf4 or Bcl-2 peptide, natural or synthetic, with a dimension less than 30 amino acids, preferably of dimension less than 20 amino acids, characterized in that said peptide specifically binds in vitro a phosphatase 2A protein holoenzyme or one of its subunits. By specifically bind, it is understood that the peptide is able to inhibit in a competitive way the binding of a viral or parasitic protein with PP2A peptides.

The invention is also concerned with a peptide comprising a 12 amino acid sequence of the *Theileria parva* Ckα 2 protein (FD6) capable of interacting with the PP2A sub-unit A and to penetrate in a Hela cell (García,A. et al. (2000) Inhibitions de processus tumoraux ou infectieux par transfert intracellulaire de peptides mimant des sites d'interaction avec la sérine /thréonine phosphatase PP2A). The invention is further concerned with the sequence corresponding to the interaction site of the PP2A with the Bα sub-unit of the PP2A 1-B site (cf. table 1). This peptide could penetrate in cells and, like the E4orf4 protein of the human adenovirus, could interact with PP2A and provoke apoptosis in cancer cells without affecting the normal cells.

The identified E4orf4 and Bcl-2 peptides, and the proposed FD6-E4orf4 peptides are particularly useful in the treatment of certain tumors, viral or parasitic infections. A person of the art may select, with the aid of competition binding assays, novel peptides, derived from identified sequences of the invention, such peptides inhibiting in a competitive way the binding of the native protein to which they derive with a PP2A holoenzyme or one of its subunits.

Thus, the invention also concerns a natural or synthetic peptide, as defined above, characterized in that it inhibit in a competitive way, the interaction of the native protein to which it derives with a PP2A holoenzyme or one of its subunits.

The peptides of the invention, on order to be efficient in vivo in the treatment of certain tumors or certain viral or parasitic infections, may be coupled to a vector capable of transferring said peptide in a eukaryotic cell. The small-dimensioned peptides of the invention allow them to pass through the cell membrane. The use of appropriate vectors further allow to target certain tissue-related peptide, certain cells, even certain specific cellular compartments, and particularly, the cytoplasm or the cell nucleus, in accordance with the desired therapeutic effect.

The invention is naturally concerned with the means allowing synthesis of the peptides of the invention. Particularly, the invention is concerned with a polynucleotide characterized in that its sequence codes for a peptide of the invention. Preferred polynucleotides are polynucleotides which their sequence is chosen from one of the following sequences:

E4 orf4 (375 bp; SEQ ID NO: 12)
```
atggcccacc atcgtctgcc ccgcgtttgt gtaaagggca ttattcattt tgaggaagat   60
tttgttagag agcttggatc aatgctggag tctcctatgg agtttctctt cgacaccatt  120
gatgatgtta ctgcttctat attttgtgaa agcatgttta aggctgttga taaaaacaag  180
cctgggatta cttttaaggt ggtcttttac tctcagcttg gttttgagta tgatgatgct  240
cttgcacatt ttaaaggcac tttaattaaa gaaatttctg acgttgttaa taatcaccct  300
aatgtaaaca atgcttttag aggaagggag attgtcactg tatctttgtt agaagtgttt  360
agtttttgtt cataa
```

Bcl-2 (618 bp; SEQ ID NO: 14)
```
atggcgcacg ctgggagaac ggggtacgac aaccgggaga tagtgatgaa gtacatccat   60
tataagctgt cgcagagggg ctacgagtgg gatgcgggag atgtgggcgc cgcgccccg   120 ggggccgccc ccgcaccggg catcttctcc tcccagcccg ggcacacgcc ccatccagcc  180
gcatcccgcg acccggtcgc caggacctcg ccgctgcaga ccccggctgc ccccggcgcc  240 gccgcgggc ctgcgctcag cccggtgcca cctgtggtcc acctggccct ccgccaagcc   300
ggcgacgact tctcccgccg ctaccgcggc gacttcgccg agatgtccag ccagctgcac  360
ctgacgccct tcaccgcgcg gggacgcttt gccacggtgg tggaggagct cttcagggac  420
ggggtgaact gggggaggat tgtggccttc tttgagttcg gtggggtcat gtgtgtggag  480
agcgtcaacc gggagatgtc gcccctggtg gacaacatcg ccctgtggat gactgagtac  540
ctgaaccggc acctgcacac ctggatccag gataacggag gctgggtagg tgcatctggt  600
gatgtgagtc tgggctga
```

It may be advantageous to synthesize a polypeptide comprising the repetition of the identified peptide motifs of the invention. Consequently, the invention concerns a polynucleotide characterized in that it consists of a multimer of said polynucleotide coding for a peptide of the invention. The invention also concerns a polypeptide characterized in that it is obtained from the repetition of a peptide of the invention.

The invention is further concerned with a cellular expression vector, characterized in that it comprises a polynucleotide as defined above and regulatory sequences allowing expression of a peptide of the invention in a host cell.

The invention is also concerned with a preparation method of a peptide according to the invention, comprising the transformation of a cell with the aid of a cellular expression vector as defined above, followed by the culture of the transformed cellular host, and the recovery of the peptide in the culture media.

The invention is further concerned with a purified monoclonal or polyclonal antibody characterized in that it is able to specifically bind to a peptide of the invention.

Antibodies specifically raised against identified peptides of the invention are obtained, for instance, by the immunization of an animal by injecting a peptide of the invention, and the recovery of the produced antibodies. A monoclonal antibody may be obtained according to methods known by one skilled in the art, such as the method described by Kohler and Milstein (1975).

The obtained antibodies, specifically raised against phosphatase 2A protein targets find their use in particular in immunotherapy. They can, for instance, serve as antagonists of viral or parasitic proteins raised against the phosphatase 2A protein so as to block the viral or parasitic development.

Furthermore, the polynucleotides coding the peptides of the invention may be directly transfered in the nucleus of the target cells, if necessary with the aid of appropriate vectors, so as to allow the in vivo expression of corresponding peptides, said peptides being likely able to block by competitive inhibition a specific interaction between the phosphatase 2A protein and the viral or cellular protein which they derive from.

Thus, the invention is concerned with a pharmaceutical composition comprising one of the elements chosen from a polynucleotide of the invention or an antibody of the invention.

The invention also concerns a pharmaceutical composition comprising one of the peptides of the invention in combination with a pharmaceutically acceptable vehicle.

Moreover, the invention is concerned with the use of a peptide of the invention, in the preparation of a medicament in the treatment of a viral or parasitic infection.

The peptides of the invention may be advantageously chosen so as to stimulate the induction of apoptosis linkec to the activation of the cellular phosphatase 2A protein. Thus, the invention also concerns the use of a peptide of the invention in the preparation of a medicament suited to induce apte apoptosis in target cells, such as tumoral cells.

Cancer results in the specific expression of proteins which their activity is regulated by the sequences of the peptides of the invention. The sequences coding the peptides of the invention may be used as probe for detecting, in a specific manner, from RNA extracts of a patient's biological sample, the tumoral development.

Furthermore, an antibody of the invention may be used for specifically recognizing peptidic sequences contained in viral or cellular proteins expressed during the tumoral development.

Thus, the invention is concerned with the use of a polynucleotide of the invention or an antibody of the invention in the in vitro diagnosis of cancers.

DETAILED DESCRIPTION OF THE INVENTION

According to a preferred embodiment of the invention, the peptide of the invention is characterized in that it consists of a fragment of a E4orf4 viral protein, a fragment of a Bcl-2 cellular protein or a fragment of the proposed Ckα2-E4orf4 peptide, said protein binding in vitro the phosphatase 2A protein, or a sequence distinguishable from said protein fragment by amino acid substitution or deletion, said sequence retaining the binding properties to the phosphatase 2A protein holoenzyme or one of its subunits.

In particular, a distinct sequence is a peptide sequence increasing the binding affinity to the phosphatase 2A protein holoenzyme or one of its subunits compared with the native sequence to which said distinct sequence derives. Another distinct sequence as defined above is a peptide sequence homologous to a peptide sequence originally identified, i.e. a sequence derived from a protein of another species than the one of the peptide sequence originally identified, and of which the primary sequence can be aligned with the peptide sequence originally identified with the aid of an optimal alignment program commonly used, such as BESTFIT (Wisconsin Genetics Software Package, Genetics Computer Group, GCG). In particular, a sequence A will be considered as being homologous to a sequence B if the sequences A and B present a homology of at least 50%, preferably 75%, after alignment of the sequences with the aid of a program such as BESTFIT. More preferably, two sequences are also considered homologous if the sequence are almost identical with the exception of some residues which may represent 10 to 20% of variability over the total sequence. Moreover, similar amino acids having similar by their chemical function (such as Arg and Lys) are considered as equivalents.

A particular preferred peptide of the invention is a fragment of the adenovirus type 2 E4orf4 protein, and more specifically a fragment of the canine adenovirus type 2 E4orf4 protein, or a sequence distinguishable from said protein fragment by amino acid substitution or deletion, said sequence retaining the binding properties to the phosphatase 2A protein holoenzyme or one of its subunits.

In a more preferred embodiment, a peptide of the invention is characterized in that it includes one of the following sequences:

A) RELGSMLE SPMEFLFDTI DDVTAS
   (SEQ. ID NO:1)

b) LGSMLE SPMEFLFDTI DDVTAS
   (SEQ. ID NO:2)

c) SMLE SPMEFLFDTI DDVTAS
   (SEQ. ID NO:3)

d) HFKGTLIKEISDVVNN
   (SEQ. ID NO:4)

-continued
E) AFRGRE VTVSLLEVFSFC
   (SEQ. ID NO:5)

f) V K K K K I K R E I K I SMLE SPMEFLFDTI DDVTAS
   (SEQ. ID NO:6)

g) ARTSPLQTPAAPGAAAGPAL
   (SEQ. ID NO:7)

h) RFATVVEELFRDGVNW
   (SEQ. ID NO:8)

i) RPLFDFSWLSLKTLLSLALVGA
   (SEQ. ID NO:9)

j) PLQTPAAPGAAAGPAL
   (SEQ. ID NO:10)

k) LFDFSWLSLKTLLSLALVGA
   (SEQ. ID NO:11)

l) a sequence distinguishable from SEQ ID NO: 1, 2, 3, 4, 5, 6, 7, 8, 9, 10 or 11 by amino acid substitution or deletion, said sequence retaining the binding properties to the phosphatase 2A protein holoenzyme or one of its subunits.

Among the peptide sequences distinguishable from SEQ ID NO: 1, 2, 3, 4, 5 or 6 by amino acid substitution or deletion, and being contemplated by the present invention, are more particularly the peptides which their sequence is enclosed in one of the sequence of the E4orf4protein, different variants of canine and human adenovirus type 2, and corresponding to the homologous sequences of these variants of SEQ ID NO: 1, 2, 3, 4, 5 or 6.

A preferred peptide according to the invention is a peptide chosen from one of the sequences SEQ ID NO:1, 2, 3, 4, 5, 6, 7, 8, 9, 10 or 11 and characterized in that its administration induces apoptosis of cells, in particular apoptosis of tumoral cells.

The invention preferably aims at the use of a peptide which its sequence derives from a fragment of the E4orf4 protein, as defined above, in the preparation of a medicament suited to inhibit a viral infection.

EXAMPLES

PP2A Purified Proteins

The trimeric PP2A1 protein has been purified to homogeneity from porcine brain.

Recombinant protein A (structural sub-unit of PP2A) expressed in bacteria.

Recombinant protein B55 (regulatory sub-unit of PP2A) expressed in bacteria.

Identification of E4orf4 and Bcl-2 Binding Sites with PP2A

We have mapped the binding sites between the E4orf4 proteins (coded by the canine adenovirus type 2) and the anti-apoptotic Bcl-2 protein with PP2A by using the <<peptides spot>> technique previously described (Frank et Overwing. (1996). Meth. Mol. Biol. 66, 149-169).

This approach is based on the use of membranes containing thereon dodecapeptides representing the whole protein of interest (E4orf4 and Bcl-2) with a two amino acid gap per peptide.

Each membrane is first saturated one hour at room temperature with TBS containing 5% skim milk powder and 3% BSA, then incubated overnight in the same buffer in the of 4 µg/ml of purified protein (sub-unit A of PP2A and PP2A1 holoenzyme).: Fifty six dodecapeptides covering the whole sequence of the E4orf4 protein and hundred-fifteen dodecapeptides covering the whole sequence of the Bcl-2 protein were synthesized and covalently bound to cellulosic membranes.

E4orf4 (SEQ ID NO: 1):
MAHHRLPRVCVKGIIHFEEDFVRELGSMLESPMEFLFDTIDDVTAFTSIF

CESMFKAVDKNKPGITFKVVFYSQLGFEYDDALAHFKGTLIKEISDVVNN

HPNVNNFTAFRGREIVTVSLLEVFSFCS.

BcI-2 (SEQ ID NO: 15):
MAHAGRTGYDNREIVMKYIHYKLSQRGYEWDAGDVGAAPPGAAPAFTPGI

FSSQPGHTPHPAASRDPVARTSPLQTPAAPGAAAGPALSPVPPVVHLALR

QAGDDFFTSRRYRGDFAEMSSQLHLTPFTARGRFATVVEELFRDGVNWGR

IVAFFEFGGVMCVESVNFTREMSPLVDNIALWMTEYLNRHLHTWIQDNGG

WVGASGDVSLG.

Figure 1:
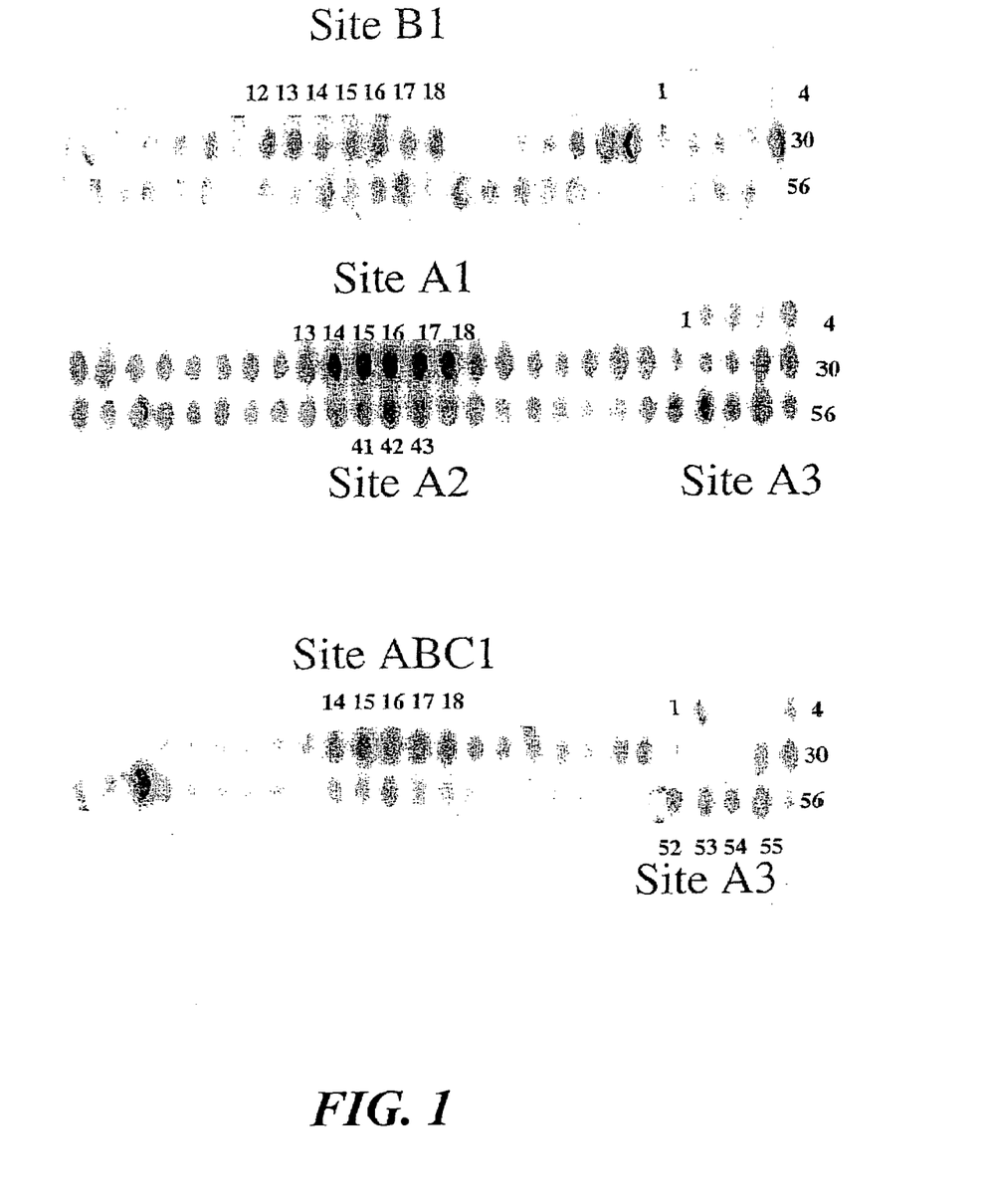
FIG. 1: Identification of binding sites of E4orf4 protein with PP2A.
Figure 2:
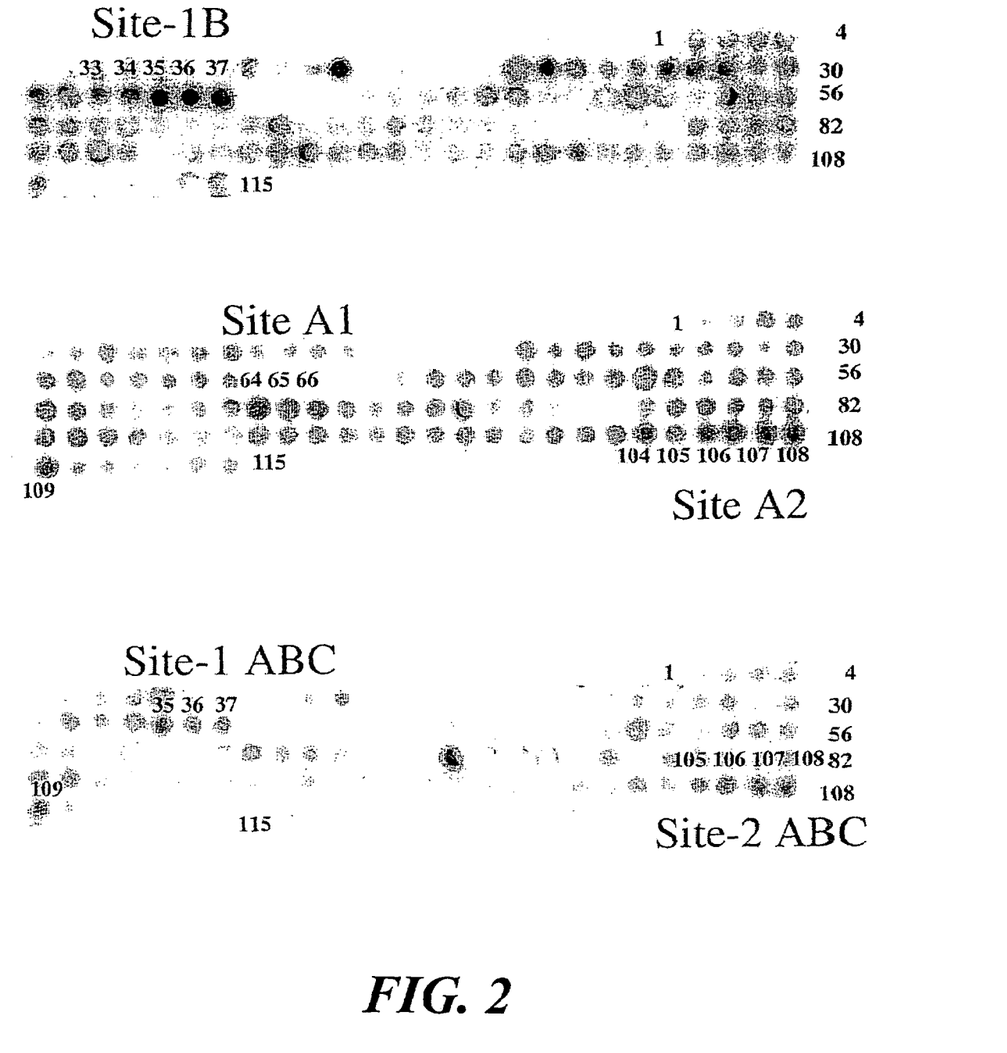
FIG. 2: Identification of binding sites of Bcl-2 protein with PP2A.

The specific interaction of each purified protein (respectively the structural sub-unit A, the regulatory sub-unit of B55(B) or the trimeric ABC holoenzyme (named PP2A1) with a peptide sequence is shown by western blot, following incubation of the membrane with an antibody raised against the structural protein A (A), the regulatory sub-unit B (B) and with a pool of antibodies recognising the A, B, and C proteins of PP2A (ABC) (FIGS. 1 and 2).

Example 1

Identification of Peptidic Sequences Containing Binding Sites of the E4orf4 Protein Coded by the Canine Adenovirus Type 2 with Proteins of the PP2A Family.

Screening of a membrane containing peptides covering the E4orf4 sequences with different forms of purified PP2A (FIG. 1) allowed us to identify five amino acid sequences containing interaction sites of E4orf4 with PP2A (cf. table 1).

We were able to respectively determine:

a peptidic sequence containing a binding site of E4orf4 with the structural sub-unit B ("site B1" corresponding to peptides 12 to 18).

Three peptidic sequences corresponding to three binding sites of E4orf4 with the sub-unit A ("site A 1" corresponding to peptides 13 to 18 and "site A2" corresponding to peptides 41 to 43 and "site A3" corresponding to peptides 52 to 55).

Two peptidic sequences corresponding to two binding sites of E4orf4 with the PP2A1 protein ("site B1" corresponding to peptides 14 to 18 and "site A3" corresponding to peptides 52 to 55).

It is interesting to note that (table 1) the B1, A1 and ABC1 sites partially overlap one another thus suggesting:

that the sub-units A and B can interact on the same site which has never been established in the PP2A system. Moreover, the interaction of the trimeric PP2A with this site requires a shorter sequence thus suggesting a conformational regulation.

TABLE 1

Binding sites of E4orf4 with different PP2A proteins

| | | |
|---|---|---|
| Site B1 | 23-RELGSMLE SPMEFLFDTI DDVTAS-46 | SEQ ID NO: 1 |
| Site A1 | 25-LGSMLE SPMEFLFDTI DDVTAS-46 | SEQ ID NO: 2 |
| Site ABC1 | 28-SMLE SPMEFLFDTI DDVTAS-46 | SEQ ID NO: 3 |
| Site A2 | 83-HFKGTLIKEISDVVNN-98 | SEQ ID NO: 4 |
| Site A3 | 106-AFRGRE VTVSLLEVFSFC-124 | SEQ ID NO: 5 |

Example 2

Identification of Peptidic Sequences Containing Binding Sites of Bcl-2 Protein with Proteins of PP2A Family.

Screening of a membrane containing peptides covering the Bcl-2 sequences with different forms of purified PP2A (FIG. 2) allowed us to identify five amino acid sequences containing interaction sites of Bcl-2 with PP2A (cf. table 2).

We were able to respectively determine:

a peptidic sequence containing a binding site of Bcl-2 with the regulatory sub-unit B ("site 1-B" corresponding to peptides 33 to 37).

two peptidic sequences containing two binding sites of Bcl-2 with the structural sub-unit A (site A1 corresponding to peptides 64-67 and site A2 corresponding to peptides 104-109).

two peptidic sequences containing a binding site of Bcl-2 with the PP2A1 holoenzyme (site 1-ABC corresponding to peptides 35 to 37 and site 2-ABC corresponding to peptides 105-109).

It is interesting to note that the 1-ABC and 2-ABC sites correspond respectively to the 1-B and A2 sites with respectively two and four amino acid gaps probably linked to a different conformation thus resulting in the interaction of proteins A and B within the holoenzyme.

Moreover, it is noteworthy that the 1-B/1-ABC site is located at the ser-70 level where the phosphorylation regulated the PP2A activity while the 2-ABC/A2 site is located at the C-terminus end of the protein. Contrary to the interaction sites with PP1, these two sites do not interfer with the BH domains of PP2A (see Garcia A. et al. PP1 et PP2A des ser/thr phosphatases au coeur de l'apoptose (2001). Med/Sci 17, 1214-1216 for general discussion).

TABLE 2

Binding sites of BcI-2 with different PP2A proteins

| | | |
|---|---|---|
| Site 1-B | 67-ARTSPLQTPAAPGAAAGPAL-86 | SEQ ID NO: 7 |
| Site A1 | 129-RFATVVEELFRDGVNW-144 | SEQ ID NO: 8 |
| Site A2 | 207-RPLFDFSWLSLKTLLSLALVGA-228 | SEQ ID NO: 9 |

TABLE 2-continued

Binding sites of Bcl-2 with different PP2A proteins

| Site 1-ABC (site 1B) | 71-PLQTPAAPGAAAGPAL-86 | SEQ ID NO: 10 |

TABLE 2-continued

Binding sites of Bcl-2 with different PP2A proteins

| Site 2-ABC (site A2) | 209-LFDFSWLSLKTLLSLALVGA-228 | SEQ ID NO: 11 |

The invention claimed is:

1. An isolated peptide with less than 30 amino acids and at least one amino acid sequence selected from the group consisting of:
RELGSMLESPMEFLFDTIDDVTAS (SEQ ID NO:1);
LGSMLESPMEFLFDTIDDVTAS (SEQ ID NO:2);
SMLESPMEFLFDTIDDVTAS (SEQ ID NO:3);
HFKGTLIKEISDVVNN (SEQ ID NO:4); and
AFRGREVTVSLLEVFSFC (SEQ ID NO:5).

2. An isolated peptide with less than 30 amino acids and at least one amino acid sequence that is at least 90% identical with a complete amino acid sequence selected from the group consisting of:
RELGSMLESPMEFLFDTIDDVTAS (SEQ ID NO:1);
LGSMLESPMEFLFDTIDDVTAS (SEQ ID NO:2);
SMLESPMEFLFDTIDDVTAS (SEQ ID NO:3);
HFKGTLIKEISDVVNN (SEQ ID NO:4); and
AFRGREVTVSLLEVFSFC (SEQ ID NO:5).

3. An isolated peptide with less than 30 amino acids and at least one amino acid sequence that is at least 90% identical with a complete amino acid
sequence selected from the group consisting of:
ARTSPLQTPAAPGAAAGPAL (SEQ ID NO:7);
RFATWEELFRDGVNW (SEQ ID NO:8);
RPLFDFSWLSLKTLLSLALVGA (SEQ ID NO:9);
PLQTPAAPGAAAGPAL (SEQ ID NO:10); and
LFDFSWLSLKTLLSLALVGA (SEQ ID NO:11).

4. A composition comprising the peptide of claim 1 and a pharmaceutically acceptable carrier.

5. A composition comprising the peptide of claim 1 coupled to a vector which can transfer said peptide into a eukaryotic cell.

6. A composition comprising the peptide of claim 2 and a pharmaceutically acceptable carrier.

7. A composition comprising the peptide of claim 2 coupled to a vector which can transfer said peptide into a eukaryotic cells.

8. The peptide of claim 1 with the amino acid sequence of SEQ ID NO:1.

9. The peptide of claim 1 with the amino acid sequence of SEQ ID NO:2.

10. The peptide of claim 1 with the amino acid sequence of SEQ ID NO:3.

11. The peptide of claim 1 with the amino acid sequence of SEQ ID NO:4.

12. The peptide of claim 1 with the amino acid sequence of SEQ ID NO:5.

13. A isolated peptide with amino acid sequence of SEQ ID NO:6.

14. The peptide of claim 3 with the amino acid sequence of SEQ ID NO:7.

15. The peptide of claim 3 with the amino acid sequence of SEQ ID NO:8.

16. The peptide of claim 3 with the amino acid sequence of SEQ ID NO:9.

17. The peptide of claim 3 with the amino acid sequence of SEQ ID NO:10.

18. The peptide of claim 3 with the amino acid sequence of SEQ ID NO: 11.

19. The peptide of claim 2, wherein the peptide specifically binds a phosphatase 2A protein holoenzyme or one of its subunits in vitro.

20. The peptide of claim 3, wherein the peptide specifically binds a phosphatase 2A protein holoenzyme or one of its subunits in vitro.

* * * * *